United States Patent [19]

Anderson

[11] 4,244,362

[45] Jan. 13, 1981

[54] ENDOTRACHEAL TUBE CONTROL DEVICE

[76] Inventor: Charles C. Anderson, 2827 W. Meadowwood Dr., Chesapeake, Va. 23321

[21] Appl. No.: 964,503

[22] Filed: Nov. 29, 1978

[51] Int. Cl.³ .................... A61M 25/00; A61M 16/00
[52] U.S. Cl. ............................... 128/200.26; 128/1.3; 128/207.14; 128/772; 128/DIG. 9
[58] Field of Search .......... 128/1.3, 1.4, 772, 348–351, 128/DIG. 9, 200.26, 207.14

[56]  References Cited
U.S. PATENT DOCUMENTS

| 2,541,402 | 2/1951 | Caine | 128/351 |
| 2,706,979 | 4/1955 | Wallace | 128/1.4 |
| 3,043,309 | 7/1962 | McCarthy | 128/348 |
| 3,314,431 | 4/1967 | Smith | 128/351 |
| 3,332,425 | 7/1967 | Luborsky et al. | 128/356 |
| 3,674,014 | 7/1972 | Tillander | 128/1.3 X |
| 3,996,939 | 12/1976 | Sheridan et al. | 128/207.14 |
| 4,063,561 | 12/1977 | McKenna | 128/351 |

Primary Examiner—Dalton L. Truluck
Attorney, Agent, or Firm—John E. Benoit

[57] ABSTRACT

An endotracheal intubation control device is disclosed which is used with a flexible tube that is tapered for insertion into the trachea of a patient. A stylet is provided having a length greater than the tubular member and of a dimension allowing passage through the member with first magnetic means attached to one end of the stylet. A second magnetic means is provided for external placement over the tracheal orifice of a patient. The stylet is flexible and is inserted into the throat of the patient and acts as a guide for subsequent insertion of the endotracheal tube over the stylet.

7 Claims, 11 Drawing Figures

ENDOTRACHEAL TUBE CONTROL DEVICE

The present invention relates generally to an endotracheal tube control device, and more specifically to a magnetically controllable stylet for assisting in the insertion of an endotracheal tube.

BACKGROUND OF THE INVENTION

In a number of medical circumstances including routine surgery and intensive care, spontaneous respiratory capability is diminished, and a breathing assist is required. This breathing assist involves the forcing of air into the lungs by positive pressure. Positive pressure ventilation is supplied by a small bag of air or oxygen mixture squeezed by an anesthesiologist or by a bellows or piston in a mechanical ventilator. To insure that the air actually goes into the lungs rather than the esophagus and stomach and to insure that an open airway is always present during surgery or mechanical ventilation in the intensive care unit, a tube is inserted into the trachea such that the distal tip is well below the vocal cords. This tube, called an endotracheal tube, may be inserted through the mouth or the nose but must bend anteriorly in the throat in order to enter the trachea and avoid the esophagus. Once the tube is in place in the trachea, a circumferential balloon-cuff above the distal tip of the endotracheal tube is inflated with air. This balloon-cuff seals the tube in the trachea by filling the area between the tracheal wall and the endotracheal tube. Such an arrangement allows positive pressure to be applied and the lungs inflated by the anesthesiologist or mechanical ventilator. The balloon-cuff also protects the trachea from any foreign material from the mouth or regurgitated from the stomach.

Ever since the endotracheal tubes were introduced, anesthesiologists and other physicians have experienced difficulties placing endotracheal tubes into the trachea, a procedure called intubation. Of all procedures done in the intensive care unit related to maintaining ventilation of critically ill patients, intubation of the trachea is associated with the greatest number of complications. Very few physicians other than anesthesiologists have any proficiency at inserting endotracheal tubes. Usually, intubation involves the use of a device called a laryngoscope.

In order to insure that the endotracheal tube goes into the airway to trachea instead of the esophagus, the anesthesiologist must visualize the vocal cords by extending the patients head slightly and by elevating the jaw of the patient with the laryngoscope. In his position behind the patient's head, he can place the tube between the vocal cords, into the trachea below. One of the principle dangers of this procedure is that it almost always requires that the patient be temporarily paralyzed. Paralysis of the patient facilitates visualization of the vocal cords by relaxing the jaw muscles and preventing the patient from retching or otherwise interfering with the placement of a large piece of metal (the laryngoscope) down his throat. Unfortunately it also eliminates any contribution that the patient might take towards his own breathing. Failure to place the endotracheal tube rapidly can result in death if the patient cannot be ventilated by a mask placed tightly over his mouth and nose in between attempts to intubate with the laryngoscope. Ventilating a patient by mask and positive pressure from a bag of oxygen also requires particular skill and practice and is nearly impossible with some patients and without proper equipment.

Even experienced anesthesiologists have difficulty intubating certain patients. Patients with the following problems are particularly difficult to intubate:

(1) short muscular neck
(2) receding jaw
(3) large, thickened tongue
(4) high arched palate
(5) cleft lip or palate
(6) cervical or temperomandibular arthritis (common in elderly patients, prevents adequate extention of the neck in order to see the vocal cords)
(7) post surgical scars or burns to the face, neck, or mouth
(8) pharngeal or laryngeal tumors
(9) inflammation of the epiglottis or tonsils
(10) facial fractures
(11) thyroid disease (colloid, goiter, substernal thyroid)
(12) deviation of the epiglottis, vocal cords, or trachea from the midline by stricture or kyphoscoliosis.

Such patients are difficult to intubate under the best of circumstances, that is, in the operating room prior to elective surgery. At this time the anesthesiologist has time and appropriate equipment and other skilled persons to give the patient 100% oxygen prior to putting him to sleep and paralyzing him. The patient can be properly positioned and counseled to know what to expect. Even if his intubation is prolonged and difficult, he is put to sleep first by intravenous medication and is not aware of the complication. Intubating patients in the intensive care unit, emergency room, coronary care unit, or elsewhere outside the operating room is much more difficult. Unlike the well-prepared, sedated, and pre-oxygenated patient on the operating room table, the intensive care patient or emergency room patient is often in great respiratory and cardiovascular distress at the time endotracheal intubation is mandatory. He may be so short of breath that he refuses to lie down or allow a tight fitting mask on his face. Time and skill are of great importance, as is experience obviously, to overcome unexpected anatomic problems in choking, suffocating, uncooperative, frightened patients. Some types of lung disease leave the lungs so stiff that adequate ventilation with a mask is not possible. Since the patient is already in respiratory distress despite the usual administration of oxygen by a loosely fitted mask, the rapid institution of an intravenous sedative and paralyzer is a gamble that an endotracheal tube can be inserted swiftly in spite of unexpected anatomical problems which could interfere with intubation, and should intubation not be successful, that an appropriate mask, oxygen source, anesthesia bag, and skill are at hand to ventilate the paralyzed patient in between intubation attempts or until more skilled persons and/or equipment are available. Should the endotracheal tube be inadvertently placed in the esophagus, the forcing of air into the esophagus can result in rupture of the stomach or, more commonly, the inducement of vomiting. Gastric contents may then go into the airway and severely damage the lungs.

Skill with a laryngoscope only comes with constant practice. It is therefore not surprising that only anesthesiologists and certain intensive care physicians are capable of intubating the trachea proficiently. On occasion, an endotracheal tube can be inserted into the nose and blindly advanced into the throat and through the vocal cords without paralyzing the patient. This technique is particularly useful in the patient with acute respiratory distress because it requires only local anesthesia to the nose and allows the patient to continue with his own breathing, although it is not totally adequate for him, during the insertion of the endotracheal tube. Obviously, this blind technique requires even more skill and practice to avoid inserting the tube into the esophagus or injuring the patient. In addition, this nasal approach is often impossible for anatomic reasons even if an experienced person is making the attempt.

These problems have been discussed in part and a proposed device disclosed in U.S. Pat. No. 4,063,561 issued Dec. 20, 1977. The device disclosed therein is a newly constructed endotracheal tube which includes therein metallic material within the walls of the tube and which may be affected by external magnetic devices placed over the larynx of the patient externally. Obviously, the cost of manufacturing individual tubes with metallic wire in the walls would be much greater than the cost of manufacturing the present invention, which can be used with any existing endotracheal tube, is reusable indefinitely, and has no expensive parts.

The above mentioned patent further discloses a possibility of enclosing frictionally a metallic block within the tube lumen which is secured to the end of a flexible wire whereby an ordinary endotracheal tube can be inserted into the throat and the entire tube manipulated by an external magnet into the trachea. All endotracheal tubes must be stiff enough to prevent excessive collapse when they bend. For this reason, normal endotracheal tubes cannot be manipulated externally with a necessarily small piece of metal within the lumen of the tube. Such an arrangement could be potentially dangerous. The block of metal could become dislodged from the wire and drop into the trachea. Further, such a metallic plug may become stuck upon its withdrawal at the point of anterior bend of the endotracheal tube in the nose or mouth, completely occluding the airway. The problems arising from this arrangement are further apparent from the fact that the emphasis in the above mentioned patent is upon the creation of a new endotracheal tube. The attraction of a magnet, no matter how large, for a piece of metal is still a function of the mass of both pieces of metal. The size of the metallic plug as illustrated in the patent cannot be large enough to manipulate a normal endotracheal tube because it must fit into the lumen of the tube. Increasing the size of the magnet outside will not overcome the distances involved or the stiffness of the ordinary tube.

The above disadvantages are overcome by the present invention wherein a very flexible stylet, instead of a whole endotracheal tube, is controlled by an external magnet by incorporating a second magnet into the distal end of the stylet. This small magnet on the distal tip of the stylet has opposite polarity to the external magnet, thus increasing their attraction and providing consistant alignment and direction toward the vocal cords. The stylet may be inserted through the mouth or nose in almost any body position and is of a dimension of fit within a standard endotracheal tube without completely occluding its lumen. After the distal tip of the stylet is within the trachea, the endotracheal tube is advanced over the stylet into the trachea, and the stylet quickly removed. Accordingly, it can be seen that the stylet acts as a flexible intubating guide for the endotracheal tube. To facilitate removal of the stylet from the endotracheal tube, the diameter of the stylet is much smaller than the lumen of the endotracheal tube. The magnet at the tip of the stylet may be constructed out of many small magnets. When stuck together, they function exactly like one long magnet, but when bent around a tight turn will articulate with one another and allow flexibility and easy withdrawal once the endotracheal tube has been advanced over the stylet into the trachea. This arrangement of many small articulating magnets functioning as one magnet is especially useful as the size of the endotracheal tube decreases. Larger endotracheal tubes do not require the articulation of small magnets at the distal tip of the stylet because there is adequate space in the lumen to withdraw the stylet without the magnet becoming lodged in the tube at its point of bend in the posterior pharynx. The flexible stylet may be inserted originally into the mouth or nose and directed into the trachea before the endotracheal tube is advanced over it, or the stylet and endotracheal tube may be advanced as a unit or alternately, as long as the stylet stays several inches in front of the tip of the endotracheal tube. In any case, once the tube has been advanced into the trachea, the stylet is quickly removed, the balloon-cuff of the tube inflated, and positive pressure ventilation initiated. Paralysis is never necessary. Local anesthetic agents may be sprayed or applied to the nose, throat, and tongue prior to insertion of the stylet. Mild sedation may be given, but the patient continues to breathe for himself and may remain in the sitting position if he desires.

Besides a system of nasal or oral tracheal intubation, the stylet is constructed to be not only very flexible and responsive to the external magnet but also to be at least twice the length of a standard endotracheal tube. This extra length provides the ability to change one endotracheal tube that may be defective or too small with a new endotracheal tube, again without paralysis or a laryngoscope. In this case the stylet is inserted (using the end opposite the magnetic tip) into the old endotracheal tube and the old tube removed when the stylet is in the trachea. Then a new tube can be advanced over the stylet and the stylet withdrawn. This procedure is rapid, does not require an external magnet, and is far safer and easier than removing the old tube and necessitating the insertion of a new tube by sedation, paralysis, and a laryngoscope. The stylet is constructed of a material which is spring-like and slides easily inside the endotracheal tube, bends easily but can be pushed, confers enough rigidity to allow guidance for an endotracheal tube, but is very responsive in a magnetic field.

Accordingly, it is the purpose of this invention to provide an endotracheal tube insertion system which does not require the risky technique of paralysis, can be used by anesthesiologists to intubate patients with difficult anatomical problems through the nose or mouth, can be used by relatively unskilled medical personnel in emergencies when an anesthesiologist is not present, can be used in a variety of positions, including supine, sitting and lateral decubitus, and can be used and reused indefinitely on standard endotracheal tubes. This endotracheal tube insertion system provides for a flexible stylet, having a magnet attached to one end, to be guided into the trachea by means of an external magnet with opposite polarity. The endotracheal tube is advanced over the stylet so as to enter the trachea with the subsequent removal of the stylet.

It is a further object of this invention to provide a stylet guiding means which may be used to quickly replace one endotracheal tube for another without paralysis or the use of a laryngoscope.

BRIEF DESCRIPTION OF THE DRAWINGS

These and other objects of the invention will become apparent from the following description when taken in conjunction with the drawings wherein.

Before proceeding with the description of the invention, reference should be made to the term "stylet" as used in the medical profession. A definition and a discussion of a stylet may be found in "Understanding Anesthesia Equipment" pages 274 and 275 authored by Jerry A. Dorsch, M.D. and Susan E. Dorsch, M.D., The Williams and Wilkins Company. In that discussion, it is stated that a stylet is a device which fits inside an endotracheal tube. It aides in directing the insertion of the tube by making the tube more rigid and allowing its shape to be changed. In the present invention, a stylet is used as herein indicated in that it is a device that fits inside an endotracheal tube and is used to help direct the tube. However, as defined herein, it is not designed to make the tube more rigid nor to change the shape of the tube. Accordingly, for the present purposes a stylet is defined as a flexible device which fits within a tube and may be passed therethrough. More specifically, the stylet of the present invention involves a flexible device having a magnet located at one end thereof. The stylet is springlike and is so constructed that it bends easily but can be pushed along its length.

BRIEF DESCRIPTION OF THE PREFERRED EMBODIMENTS OF THE INVENTION

Figure 1:
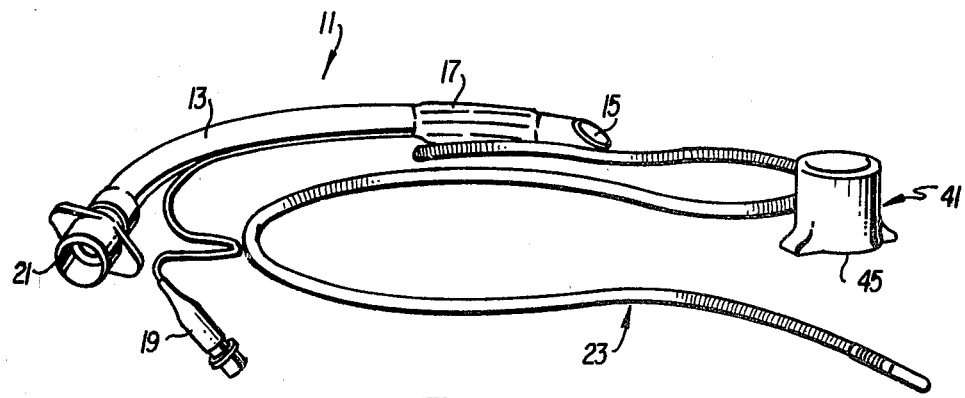
FIG. 1 is a perspective view of the three components preferably used with the present invention.

Turning now more particularly to the drawings, there is shown in FIG. 1 the three items which may be used in performing an intubation of the trachea using the stylet of the present invention. As illustrated, a standard endotracheal tube 11 comprising a plastic tube body 13 has a beveled insertion end 15 and an inflatable balloon 17. The balloon is inflated in a standard manner by the inflating syringe 19. The opposite end of the tube 13 terminates in a connector which may be secured to a breathing assist system. This is all known equipment used in the standard procedure as described hereinabove. The present invention provides a stylet 23, which will be more specifically shown and described as the description proceeds, and an exterior magnet 41. Magnet 41 is preferably a housing of plastic material 43 having a magnet secured therein with one end having a concave face 45.

Figure 2:
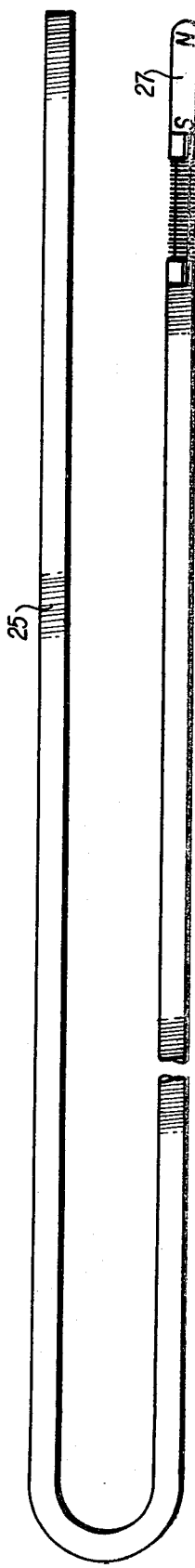
FIG. 2 is a perspective view of one embodiment of the stylet of the present invention.

Turning now more specifically to FIG. 2, there is illustrated one embodiment of a stylet of the present invention. This stylet is most useful with endotracheal tubes having an internal diameter larger than 8.0 mm.

The main body 25 of the stylet is comprised of a coiled spring of a non-magnetic material such as stainless steel or other non-magnetic material. Such a tube could be constructed of a suitable plastic material manufactured so as to conform to the characteristics of a coiled spring. A magnet 27 is secured to the other end of the spring. Magnet 27 may be encased within an inert housing 29 (FIG. 3) such as stainless steel, plastic etc., which is then secured to one end of stylet 25 by means of a weld or adhesive or the like.

Figure 3:
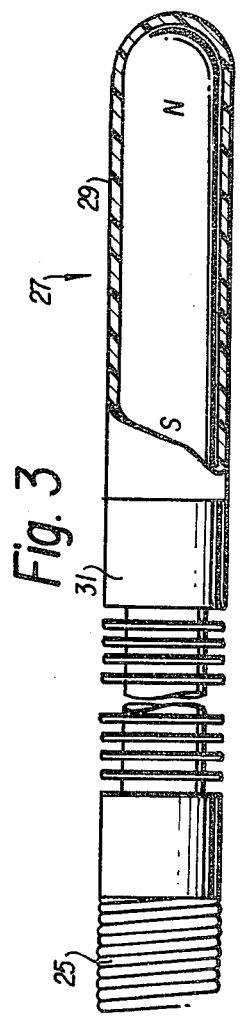
FIG. 3 is an enlarged view of a section of the stylet of FIG. 2.

FIG. 3 is an enlarged partial illustration indicating the spring bellows 31 which is secured between the housing 29 and the body 25 of the stylet. Such bellows are commercially available and provide additional flexibility at the distal end of the stylet. This further aids the ability of the distal end to bend as shown in the dotted lines of FIG. 2 when it is subjected to exterior magnetic forces.

Figure 4:
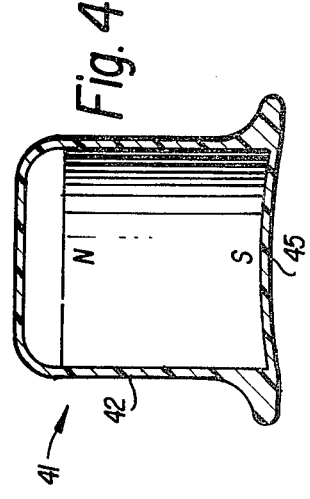
FIG. 4 is a sectional view of one embodiment of the external magnet used with the stylet of the present invention.

FIG. 4 shows one embodiment of exterior magnet 41. The magnet may be encased in an inert housing 42 of a material such as plastic or the like. As indicated, one face of housing 42 is concave for purposes which will become apparent as the description proceeds.

Figure 5:
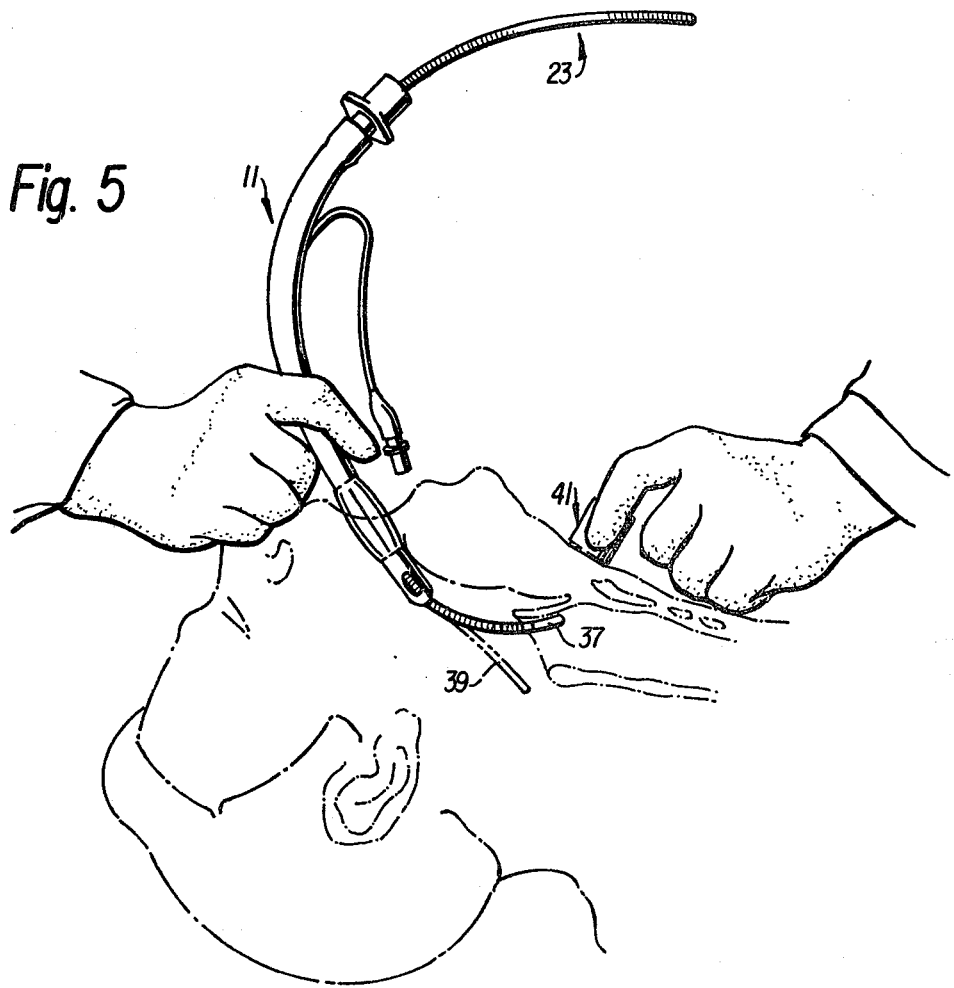
FIGS. 5, 6 and 7 illustrate the steps which are taken in using the present device for performing intubation orally.
Figure 6:
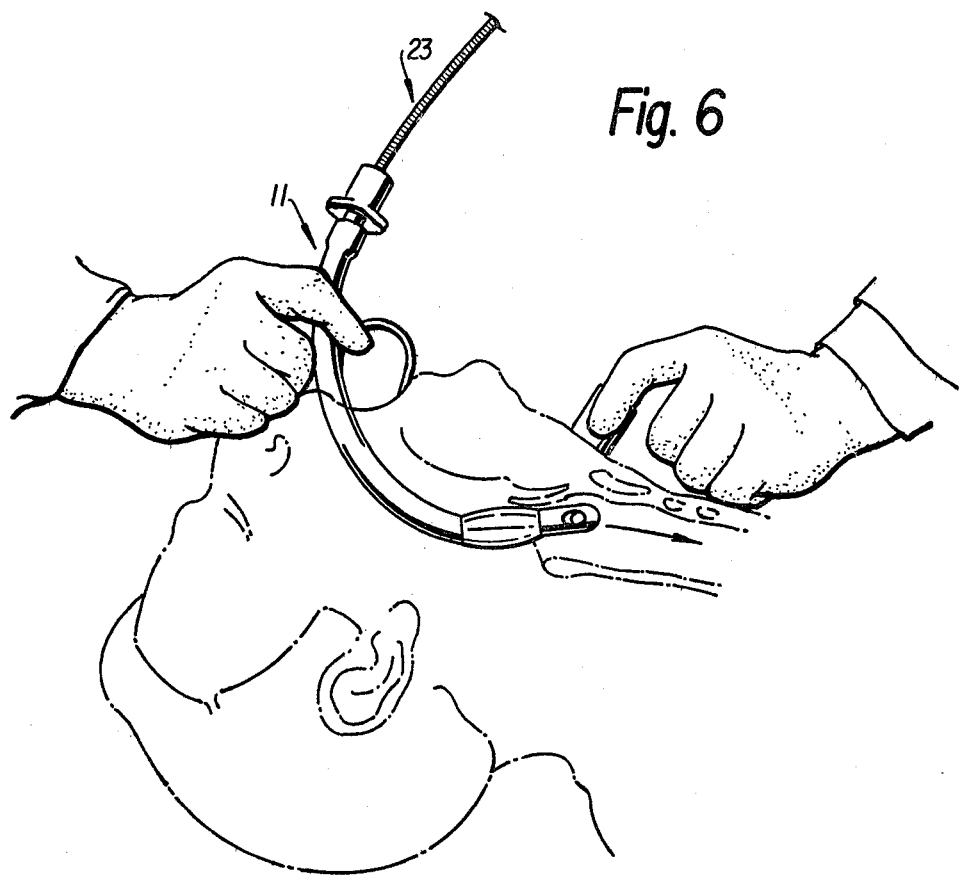
Figure 7:
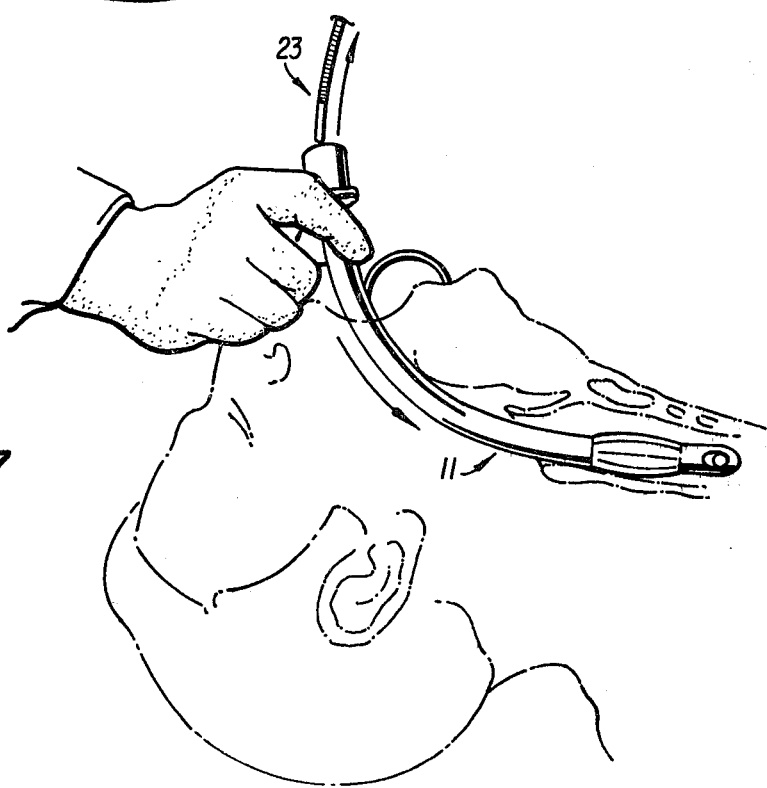

FIGS. 5, 6 and 7 illustrate the use of the device when intubation is practiced orally. FIG. 5 shows the stylet 23 being inserted with the magnetic end entering into the throat of the patient. When the stylet is so inserted, the end will assume a position approximately as shown in the dotted lines 39. If allowed to follow this course, the stylet will tend to enter the esophagus instead of the trachea. However, as indicated, the magnet 41 is placed exteriorly in the midline adjacent to the prominence of the thyroid cartilage, or "Adam's Apple". This is easily distinguishable on the patient and places the magnet in a proper spot for attracting the magnetized end of the stylet 37 into the tracheal passage as indicated in the solid line form. As shown in FIG. 6, the stylet is then inserted into the tracheal cavity by sliding it along inside the endotracheal tube. The tube is then guided along by the stylet as shown until it, too enters the tracheal passage. The stylet is then removed as shown in FIG. 7, leaving the endotracheal tube in position with the trachea.

Figure 8:
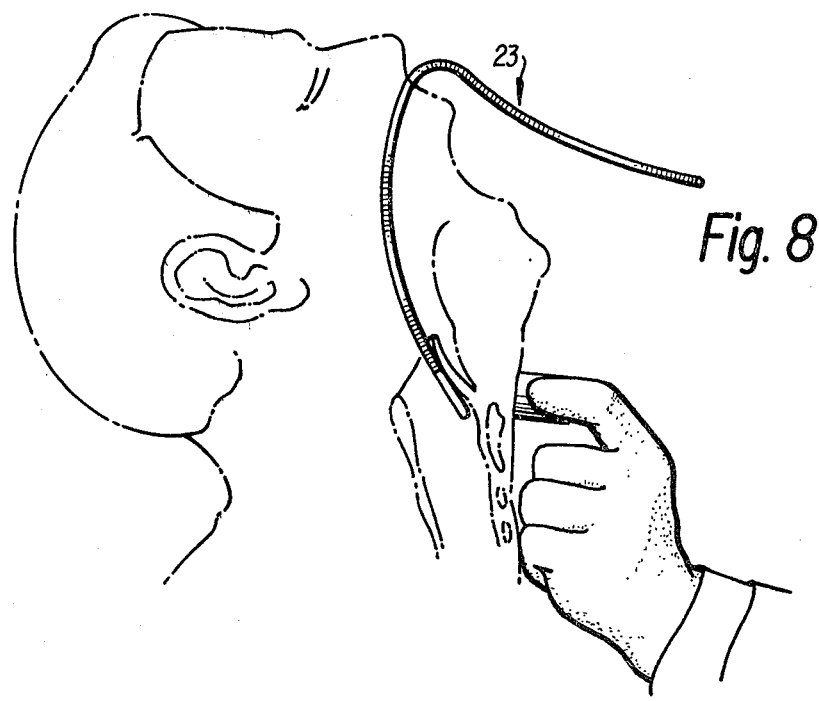
FIGS. 8 and 9 show like steps which are taken when the insertion is through the nostril.
Figure 9:
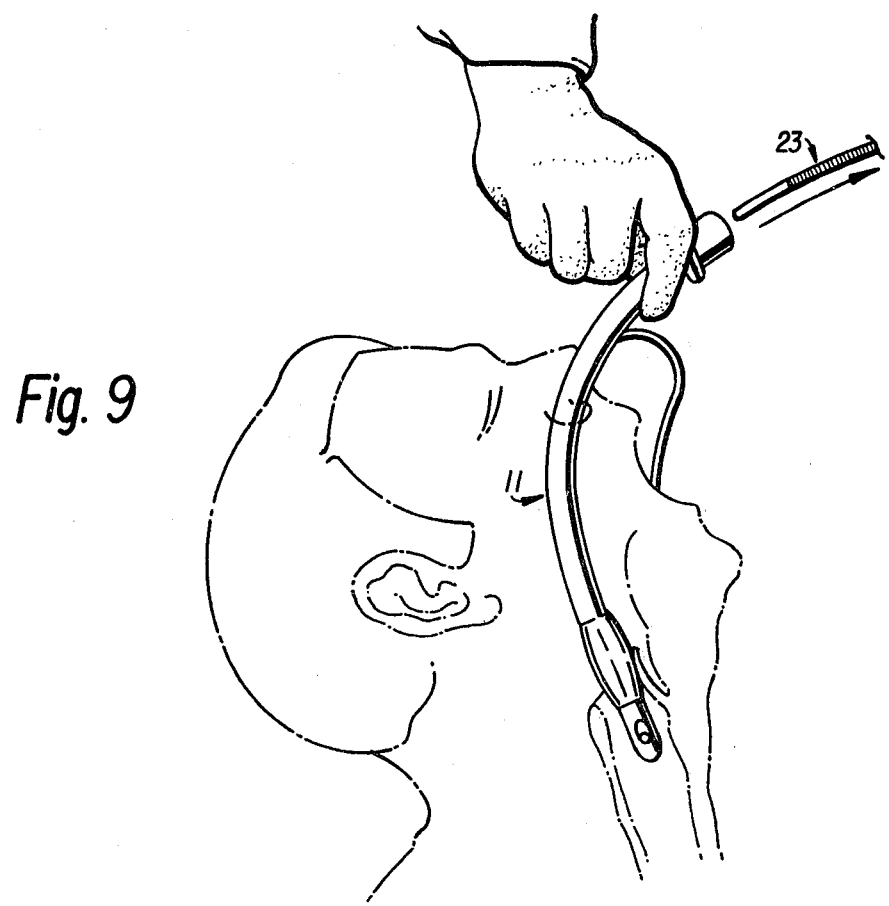

FIGS. 8 and 9 illustrate that the same procedure may be used when the nostril is dilated and the stylet and the tube may then be inserted therethrough following the same procedure for locating the stylet and, subsequently, the endotracheal tube into position.

Figure 10:
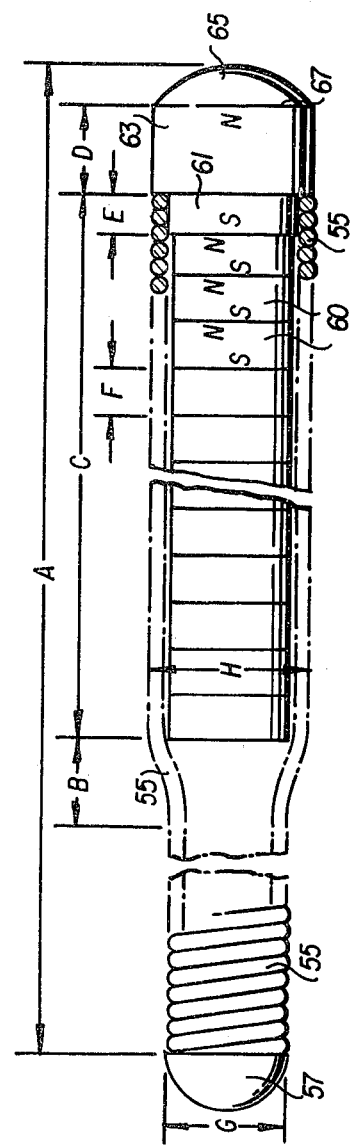
FIG. 10 is a sectional view of a further embodiment of the stylet of the present invention.
Figure 11:
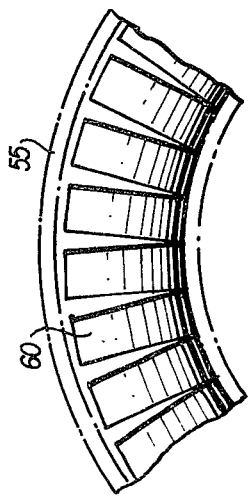
FIG. 11 shows the interaction between individual magnets used in the stylet of FIG. 10.

Turning more specifically to FIGS. 10 and 11, there is shown therein an alternate embodiment of the stylet of the present invention. The main body of the stylet is comprised of a similar coiled spring 55 which extends substantially the length of the stylet. A rounded cup 57 of an inert material such as teflon may be secured within one end of the coiled spring 55 by means of an adhesive or the like. The other end of coiled spring 55 has inserted therein a series of small magnets beginning with magnet 59 at one end and terminating at the other end with magnets 60 and 61. These magnets have a diameter slightly smaller than the internal diameter of the section of coil spring 55 which encases them. Spring 55 is made larger at this section to allow the magnets to interact as shown in FIG. 11. The magnets terminate in a larger magnet 63 which has a reduced section 61 which fits within the end of the coil spring and is secured thereto by means such as by soldering or with an adhesive. Also, to provide a smooth insertion area, an inner hemispherical segment 65 is secured to the outer end of magnet 63 by means such as an adhesive. In order to present the stylet in an understandable dimensional view, the following parameters are typical of a desired stylet.

| DIMENSION | PARAMETER-INCHES |
| --- | --- |
| A | 27 |
| B | ¼ |
| C | .8125 |
| D | ⅛ |
| E | 1/16 |
| F | 1/16 |
| G | 3/16 O.D. |
| H | ¼ O.D. |

FIG. 11 illustrates one of the reasons for providing the separate individual magnets as shown in FIG. 10. While the magnets do not totally part from each other because of the extreme force exerted between them, they may partially separate as illustrated in FIG. 11. This partial separation allows the terminal end of the stylet having the magnets to provide more flexibility and, thus, greater ease in drawing the stylets into the tracheal passage. This embodiment, when using the stylet with smaller diameter endotracheal tubes, allows the small magnets to function as one magnet, but articulate with each other, whereby the removal of the stylet from the smaller endotracheal tube is greatly eased. One of the reasons why this invention is now practical is due to the development of extremely high magnetic material such as cobalt and the like. This reduces the necessary size of the magnets while still realizing the necessary magnetic force, since the use of a magnetic material such as cobalt in the stylet itself increases the attraction between the exterior magnet and the end of the stylet to a very large degree. The use of only a metallic material for a stylet would reduce the ability to direct the end of the stylet into the trachea.

The above description and drawings are illustrative only since material substitution and dimension variations are possible without departing from the invention. Accordingly, the invention is to be limited only by the scope of the following claims.

I claim:

1. An endotracheal intubation assembly comprising
    a flexible intubating guide stylet;
    first magnetic means attached to one end of said stylet and movable therewith;
    an open ended flexible endotracheal tube having a lumen of a dimension substantially greater than the cross-sectional dimension of said stylet and said first magnetic means whereby said tube is freely movable over said stylet and said magnetic means, thereby permitting free flow of breathable gas along said lumen; and
    second magnetic means externally placeable over the tracheal orifice of a patient;
    whereby said one end of said stylet is inserted into the throat of said patient, with said first magnetic means being directed onto the trachea by said second magnetic means which is placed adjacent the external surface of said tracheal orifice area, and said endotracheal tube is threaded over said stylet and guided into the trachea by said stylet.

2. The device of claim 1 wherein said stylet comprises
    a spring coil member having said first magnetic means secured to one end thereof.

3. The device of claim 1 further comprising
    a spring bellows connected between said stylet and said first magnetic means.

4. The device of claim 2 further comprising
    a spring bellows connected between said spring coil member and said first magnetic means.

5. The device of claim 1 wherein said stylet comprises a tubular plastic flexible member.

6. The device of claim 1 wherein said magnetic means comprises
    a plurality of magnets having their poles arranged for adjacent magnetic attraction whereby articulation may occur between adjacent magnets.

7. The device of claim 1 further comprising
    means providing a substantially smooth arcuate termination at the distal end of said first magnetic means.

* * * * *